US007759550B2

(12) United States Patent
Mozsár et al.

(10) Patent No.: US 7,759,550 B2
(45) Date of Patent: Jul. 20, 2010

(54) CAULIFLOWER PLANTS HAVING A LONG STEM

(75) Inventors: József Mozsár, Osca (HU); Simon Groen, Enkhuizen (NL); Peter Tjeertes, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 825 days.

(21) Appl. No.: 11/447,563

(22) Filed: Jun. 6, 2006

(65) Prior Publication Data
US 2006/0277637 A1 Dec. 7, 2006

Related U.S. Application Data

(60) Provisional application No. 60/687,768, filed on Jun. 6, 2005.

(51) Int. Cl.
*A01H 1/00* (2006.01)
*A01H 5/00* (2006.01)
(52) U.S. Cl. ........................................ 800/306; 800/260
(58) Field of Classification Search .............. 800/260, 800/266, 268, 269, 306
See application file for complete search history.

(56) References Cited

U.S. PATENT DOCUMENTS

2005/0055744 A1* 3/2005 Quiros et al. ............... 800/284

OTHER PUBLICATIONS

Csizinszky. 1995. Proc. Fla. State Hort. Soc. 108: 178-181.*
McLaren. 2000. Alternative & Integrative Medical Society, University of British Columbia, Volumn II, Issue III, p. 4.*
Baggett et al. 1995. J. Amer. Soc. Hort. Sci. 120(2): 292-296.*
Bouckerie. 2001. Unilet Information, No. 107.*
Watts. 1963. Euphytica 12: 323-340.*
Nieuwhof. 1958. Euphytica 7: 170-178.*
Csizinszky. Proc. Fla. State Hort. Soc. 108: 178-181, 1995.*
McLaren. Alternative & Integrative Medical Society, University of British Columbia, vol. II, Issue III, Winter 2000, p. 4.*
P.J. Salter, "Meeting the call for mini-cauliflowers," *Commercial Grower*, pp. 635-636, May 22, 1970.
K.F. Thompson, "Cabbages, kales etc.," Evolution-of-crop-plants, Simmonds-NW (ed), pp. 49-52, 1976.
H.G. Paths and G.P. Gent, "Sweetcorn and Broccoli—New Varieties for the Processor," *The Grower*, pp. 1116-1118, May 27, 1976.
Von Jürgen Kirschke and Hermann J. Heege, "Plant morphology and harvesting technique with head cabbage," Pflanzenmorphologie und Erntetechnik bei Kopfkohl, Gemuse, 14(5), pp. 174-178, 1978.
M.H. Dickson and C.Y. Lee, "Persistent White Curd and Other Curd Characters of Cauliflower," *J. Amer. Soc. Hort. Sci.*, 105(4), pp. 533-535, 1980.
C.A. Mullins et al., "Performance of New Broccoli and Cauliflower Cultivars in Tennessee," *Tennessee Farm and Home Science*, pp. 23-24, Jul., Aug., Sep. 1980.

S.A. Harmon and M.E. Austin, "'Georgia Upright' Collard," *HortScience*, 16(4), p. 571, Aug. 1981.
J.R. Baggett and D. Kean, "Broccoli Breeding Lines OSU 101-OSU 115," *HortScience*, 20(4), pp. 782-784, Aug. 1985.
J.R. Baggett and D. Kean, "Clubroot-resistant Broccoli Breeding Lines OSU CR-2 to OSU CR-8," *HortScience*, 20(4), pp. 784-785, Aug. 1985.
M.H. Dickson, "Male Sterile Persistent White Curd Cauliflower NY 7642 A and its Maintainer NY 7642B," *HortScience*, 20(5), p. 957, Oct. 1985.
H.P. Mishra and B.P. Singh, "Studies on the Nutrients and Growth Regulator Interaction in 'Snowball-16' Cauliflower (*Brassica oleracea* Var. *Botrytis*)," *Prog. Hort.*, 18(1-2), pp. 77-82, 1986.
L.R. Walton and J.H. Casada, "Evaluation of Broccoli Varieties for Mechanical Harvesting," *Applied Engineering in Agriculture*, 4 (1), pp. 5-7, Mar. 1988.
L.A. Nozadze and G.A. Bakashvili, "Cabbage cultivars for mechanical harvesting," Kartofel'-i-Ovoshchi, No. 5, pp. 28-29, 1989. CAB Abstract Ideal Borzhomi, Yuzhanka 31, -Khar'kovskaya Zimnyaya and Moldavskaya are the cultivars most suited to mechanical harvesting in Georgia. They are highly productive (45.0-52.5 t/ha), uniformly maturing, and resistant to diseases and mechanical injury, and they have firm heads, optimum stem height and good transport and storage properties.
James R. Baggett et al., "Inheritance of Internode Length and its Relation to Head Exsertion and Head Size in Broccoli," *J. Amer. Soc. Hort. Sci.*, 120(2), pp. 292-296, 1995.
T.A. Bon, Agricultural and Biosystems Engineering Department, North Dakota State University, Fargo, North Dakota, "Senior Design Project Development of a Non-Selective Broccoli Harvester," Paper No. 97-1018, 1997 ASAE Annual International Meeting Sponsored by ASAE, Minneapolis Convention Center, Minneapolis, Minnesota, Aug. 10-14, 1997.
Paulo Eduardo de Melo and Leonardo de B. Giordano, "'Ramoso de Brasilia': nova cultivar de couve-brócolos," *Hortic. bras.*, pp. 17 (2), pp. 172-173, Jul. 1999.
"All over broccoli," *Grower*, p. 23, Jul. 27, 2000.
Richard Bouckerie, "Cauliflower Broccoli, Machine harvest becomes possible," *Unilet Information*, No. 107, Jan. 2001.

(Continued)

*Primary Examiner*—David H Kruse
*Assistant Examiner*—Keith O. Robinson
(74) *Attorney, Agent, or Firm*—S. Matthew Edwards

(57) ABSTRACT

The present invention relates to novel *brassica* plants, in particular to novel cauliflower plants. In one embodiment, the novel cauliflower plants provided herein comprise a long stem and are suitable for mechanical harvesting. The application also further discloses seeds the cauliflower plants of the present invention and parts thereof, for example pollen, ovules and curds. The application also further discloses methods of using a plant of instant invention, such as methods of producing a cauliflower curd of the instant invention, and methods of harvesting the curds of plants of the instant invention.

8 Claims, No Drawings

OTHER PUBLICATIONS

M.S. Kanwar and B.N. Korla, Comparison of biparental and $F_3$ progenies in late cauliflower (*Brassica oleracea* var. *botrytis* L.), *Himachal Journal of Agricultural Research*, 27 (1&2), pp. 36-41, 2001.

Sanjeev Kumar and B.N. Korla, "Genetic variability, heritability and genetic advance for yield and its contributing traits in late cauliflower (*Brassica oleracea* var. *botrytis* L.)," *Himachal Journal of Agricultural Research*, 27 (1&2), pp. 114-116, 2001.

Sanjeev Kumar et al., "Implications of Combining Ability in Cauliflower (*Brassica oleracea* var. *botrytis* L.)," *Crop Improv.*, 29(1), pp. 85-89, 2002.

Naveen Garg et al., Studies on Combining Ability and Gene Action in Indian Cauliflower (*Brassica oleracea* I. var. *botrytis* L.), *Crop Improv.*, 30(2), pp. 169-176, 2003.

J.C. Thakur et al., "Studies on Gene Action in Cauliflower," *Crop Improv.*, 31(1), pp. 71-74, 2004.

A.J. Bhuyan, "Maturity Indices and Harvesting of High Value Crops," [online], pp. 1-6, Retrieved from the Internet: URL:http://www.dae.gov.bd/NCDP/docs/tot_course_3.2.7/pdf.

Steven T. Koike et al., "Cauliflower Production in California," [online], pp. 1-3, Retrieved from the Internet: http://anrcataloq.ucdavis.edu/pdf/7219.pdf.

"Cauliflower Power, World's first automated cauliflower harvesting system is set for commercial production," [online], Retrieved from the Internet: http://www.ost.gov.uk/link/linkcasestudies/cauliflowersapril03.pdf.

Linda Naeve, Department of Horticulture, Iowa State University, "Growing Cauliflower," [online] Retrieved from the Internet: http://www.ipm.iastate.edu/ipm/hortnews/1997/2-28-1997/cauliflower.html.

A.B.C. Metal, Route de lihons—80131 Harbonières—France, Sales Brochure, "Fully Mechanical Broccoli Picker".

A.B.C. Metal, Route de lihons—80131 Harbonires—France, Sales Brochure, "The broccoli picker-harvester".

L.R. Walton and J.H. Casada, "Evaluation of Broccoli Varieties for Mechanical Harvesting," Paper, American-Society-of-Agricultural-Engineers, 1986, No. 86-6544, 7pp.

* cited by examiner

CAULIFLOWER PLANTS HAVING A LONG STEM

CROSS-REFERENCE TO RELATED APPLICATIONS

This application claims the benefit of U.S. Provisional Application No. 60/687,768, filed Jun. 6, 2005. The above application is incorporated herein by reference in its entirety.

FIELD OF THE INVENTION

The present invention relates to novel *brassica* plants, in particular to novel cauliflower plants. The present invention also relates to seeds and parts of said plants, for example curds. The present invention also relates to methods of making and using such plants.

BACKGROUND OF THE INVENTION

Cauliflower (*Brassica oleracea* var. *botrytis*) is a member of the Cruciferae (mustard) family and is an important crop grown worldwide. The world production of cauliflower is close to 5 millions tons a year, covering an area of around 300,000-400,000 hectares. The edible part of the plant is the head, also called curd, which comprises of the arrested inflorescence and floral meristems. Cauliflower is an appreciated vegetable because of its pleasant taste and nutritive value. The per capita consumption of fresh cauliflower in the United States was estimated at 0.73 kg in 1982 (see e.g. Ib Libner Nonnecke, Vegetable Production, 1989, Van Nostrand Reinhold, N.Y. Publisher, pp. 382-394). However, cauliflower is a difficult crop to grow. It has very precise climatic requirements, which, if ignored, cause failure or partial failure under field conditions.

The cauliflower curd is very delicate and easily damaged, and is exclusively harvested by hand. This is however inefficient and costly, and it is estimated that 30-50% of the production costs for cauliflower are harvesting costs. Attempts have been made to harvest cauliflower curds mechanically, but they have faced difficulties in identifying the mature curds and detaching them from the plant without damaging the curds. Recently, a mechanical harvester specifically designed for cauliflower was described. This mechanical harvester uses sensor technology and image processing (see HortLINK Caulicut project, http://www.ost.gov.uk/link/linkcasestudies/cauliflowersapril03.pdf). However, the cost of the machines was reported to be high. This would require a substantial upfront investment, and it remains to be seen whether the prototypes described will be commercially successful.

There is therefore an unfulfilled need to reduce costs of production for cauliflower. In particular, there is an unfulfilled need for developments allowing increased efficiency and reductions in the costs of harvesting marketable cauliflower curds.

SUMMARY OF THE INVENTION

The instant application addresses the unfulfilled needs to increase the efficiency and to reduce the production costs for cauliflower, in particular to reduce costs of harvesting of cauliflower curds. To address these needs, the instant invention provides novel cauliflower plants with a special stem structure, especially cauliflower plants comprising a long stem. In one embodiment, the cauliflower plants of the present invention are suitable for mechanical harvest.

In one embodiment, the stem of a plant of the present invention is longer than that of currently existing cauliflower plants having commercially desirable attributes, such as capable of producing a marketable curd, and requiring approximately the same number of growing days to reach maturity. In one embodiment, the stem of a plant of the present invention is longer than that of currently existing cauliflower plants in the same cycle having commercially desirable attributes, such as capable of producing a marketable curd.

The feature of elongated stems offers the advantage of providing enough room between the ground and the bottom of the curd and thus facilitates the harvest of the curds. The feature of elongated stems also allows economical and efficient mechanical harvesting of the curd, while minimizing the risk of damage by miscutting and soil contamination of the curd. This is particularly useful for cauliflower plants of shorter cycles, which tend to grow shorter stems. Accordingly, in one embodiment, a cauliflower plant of the instant invention is a plant of the short cycle or medium cycle.

In one embodiment, a plant of the instant invention further comprises a trait of loose foliage. In one aspect, the total leaf weight of a plant of the instant invention is lower than the total leaf weight of currently existing cauliflower plants having commercially desirable attributes, such as capable of producing a marketable curd. In another aspect, the leaf volume index of a plant of the instant invention is smaller than the leaf volume index of currently existing cauliflower plants having commercially desirable attributes, such as capable of producing a marketable curd. Plants with loose foliage allow for faster, more convenient and more efficient harvesting of the curds, and reduce the risk of jamming a mechanical harvester during harvest.

In one embodiment, the average internode length of the stem of a plant of the present invention is longer than that of currently existing cauliflower plants having commercially desirable attributes, such as capable of producing a marketable curd. The feature of longer internodes offers the advantage of providing longer stems while maintaining a low number of leaves on the stem or reducing the number of leaves on the stem.

In one embodiment, a plant of the instant invention further comprises a trait of a persistent white curd. The trait of persistent white curd prevents or slows down cauliflower curds from turning yellow when exposed to sunlight, in particular in plants with curds that are not covered or only partially covered by inner leaves, for example plants with a loose foliage.

In one embodiment, a plant of the instant invention is a cauliflower plant having commercially desirable attributes. In one embodiment, a plant of the instant invention is a cauliflower plant is capable of producing a marketable curd. In one embodiment, the curd of a cauliflower plant of the present invention is used for fresh market consumption and in the processing industry.

In one embodiment, a plant of the present invention is an inbred line or a hybrid. In one embodiment, a plant of the instant invention is a dihaploid. In one embodiment, an inbred line of the present invention is a dihaploid. In one embodiment, at least one of the parents of a hybrid of the instant invention is a dihaploid. Dihaploid plants allow for high levels of uniformity of the plants of the instant invention. In one embodiment, a plant of the instant invention is capable of producing a curd that can be commercialized on the market.

In one embodiment, a plant of the present invention comprises any combination of the traits of long stem, long internodes, number of internodes, loose foliage, low total leaf weight, small leaf volume index, and persistent white curd, and short or medium cycle and uniformity, as described herein. In one embodiment, a plant of the present invention comprises a long stem, loose foliage and persistent white curd, as described herein. In one embodiment, such plant is of the short cycle or medium cycle.

The application further discloses seeds the cauliflower plants of the present invention and parts thereof, for example cells, pollen, ovules and curds. The present application also further discloses methods of using a plant of instant invention, such as methods of producing a cauliflower curd of the instant invention, and methods of harvesting the curds of plants of the instant invention. The present application also further discloses methods of producing seeds of a cauliflower plant of the instant invention, and methods of vegetatively propagating a cauliflower plant of the instant invention.

In one embodiment, a plant of the instant invention is obtained by crossing a cauliflower plant with a broccoli plant, and selecting a plant comprising a long stem. Accordingly, in one embodiment, the instant application also provides methods of producing a cauliflower plant of the present invention comprising crossing a cauliflower plant with a broccoli plant and selecting for plants comprising a long stem. In one embodiment, the method further comprises selecting for characteristics of a cauliflower curd. In one embodiment, the instant invention further provides plants obtained by such methods.

In one embodiment, the instant application also provides methods for producing a cauliflower plant comprising a long stem comprising crossing a cauliflower plant and a plant of line 03P001, representative seed of which being deposited under accession number NCIMB 41228, and selecting a plant comprising a long stem. In one embodiment, the instant invention further provides cauliflower plants obtained by such methods.

The plants of the present invention make the harvest of cauliflower curds by hand easier and faster, and thus more efficient. In one embodiment, the plants of the present invention also allow mechanical harvest of the curds using fully automatic or semi-automatic harvesters. Simple and inexpensive machinery can be used with the plants of the present invention, while keeping losses caused by miscutting and contamination with soil particles to a minimum. Harvest costs for cauliflower curds, and thus production costs for cauliflower can be accordingly reduced.

The invention therefore provides:

A cauliflower plant comprising at maturity a stem with an average internode length of at least 1.25 cm. In one embodiment, the average internode length is at least 1.30 cm, at least 1.35 cm or at least 1.40 cm. In one embodiment, the average internode length is 1.25 cm to 2.00 cm. In one embodiment, the stem comprises 18 internodes to 26 internodes, 19 internodes to 25 internodes, or 20 internodes to 24 internodes. In one embodiment, the average internode length and the number of internodes are measured when the plant is grown under conditions representative for a continental climate, e.g. in Ocsa, Hungary, and planted during the 4$^{th}$ week of May and transplanted during the 5th week of June.

The invention further provides:

A cauliflower plant comprising at maturity a stem with an average internode length of at least 80% of the average internode length of a plant of line 03P001, representative seed of which being deposited under accession number NCIMB 41228. In one embodiment, the average internode length is at least 85% or at least 90% of the average internode length of a plant of line 03P001. In one embodiment, the average internode length is 80% to 140% of the average internode length of a plant of a plant of line 03P001. In one embodiment, the number of internodes of said plant is less than 120%, less than 115% or less than 110% of the number of internodes of a plant of line 03P001. In one embodiment, the number of internodes of said plant is 80% to 120% the number of internodes of a plant of line 03P001.

The invention further provides:

Any one of the cauliflower plants above, wherein the stem length of said plant is at least 85% or at least 90% of the stem length of a plant of line 03P001, representative seed of which being deposited under accession number NCIMB 41228. In one embodiment, the stem length is 85% to 130% of the stem length of a plant of line 03P001.

The invention further provides:

Any one of the cauliflower plants above, wherein the plant is a plant of the short cycle or of the medium cycle.

The invention further provides:

A cauliflower plant comprising at maturity a stem with a length of at least 22.5 cm, when said plant is grown under conditions representative for a continental climate, e.g. in Ocsa, Hungary, and planted during the 3$^{rd}$ week of May and transplanted during the 3$^{rd}$ week of June or when said plant is grown under conditions representative for a Mediterrenean climate, e.g. in Murcia, Spain, and planted during the 1$^{st}$ week of August and transplanted during the 1$^{st}$ week of September, wherein said cauliflower plant is a plant of the short cycle or of the medium cycle. In one embodiment, the length of said stem is at least 25 cm. In one embodiment, the length of said stem is 22.5 cm to 35 cm.

The invention further provides:

A cauliflower plant comprising at maturity a stem with a length of at least 30 cm, when said plant is grown under conditions representative for a continental climate, e.g. in Ocsa, Hungary, and planted during the 4th week of May and transplanted during the 5th week of June, wherein said cauliflower plant is a plant of the short cycle or of the medium cycle. In one embodiment, the length of said stem is at least 32.5 cm. In one embodiment, the length of said stem is 30 cm to 45 cm.

The invention further provides:

Any one of the cauliflower plants above, wherein a stem of said plant comprises 18 internodes to 26 internodes, 19 internodes to 25 internodes, or 20 internodes to 24 internodes.

The invention further provides:

A cauliflower plant comprising at maturity a stem with a length of at least 85% of the stem length of a plant of line 03P001, representative seed of which being deposited under accession number NCIMB 41228, wherein said plant is a plant of the short cycle or of the medium cycle. In one embodiment, the stem is at least 90% of the length of a stem of a plant of line 03P001. In one embodiment, the length of said stem is 85% to 130% of the length of a stem of a plant of line 03P001.

The invention further provides:

Any one of the cauliflower plants above, wherein the number of internodes of said plant is less than 120%, less than 115% or less than 110% of the number of internodes of a plant of line 03P001, representative seed of which being deposited under accession number NCIMB 41228. In one embodiment, the number of internodes of said plant is 80% to 120% the number of internodes of a plant of line 03P001.

The invention further provides:

Any one of the cauliflower plants above, wherein the total leaf weight of said plant is less than 150%, less than 140%, less than 130%, less than 120% or less than 110% of the total leaf weight of a plant of line 03P001, representative seed of which being deposited under accession number NCIMB 41228. In one embodiment, the total leaf weight of said plant is 80% to 150% of the total leaf weight of a plant of line 03P001.

The invention further provides:

Any one of the cauliflower plants above, wherein the leaf volume index of said plant is less than 130%, less than 125, less than 120% or less than 110% of the leaf volume index of a plant of line 03P001, representative seed of which being deposited under accession number NCIMB 41228. In one embodiment, the leaf volume index of said plant is 80% to 130% of the leaf volume index of a plant of line 03P001.

The invention further provides:

Any one of the cauliflower plants above, wherein the plant is an inbred line, a hybrid or a dihaploid. In one embodiment, the plant is male-sterile. In one embodiment, the plant is obtainable by crossing a broccoli plant with a cauliflower plant.

The invention further provides:

Any one of the cauliflower plants above, wherein the plant comprises the genetic background of line 03P001, representative seed of which being deposited under accession number NCIMB 41228. A cauliflower plant exhibiting a stem structure as described above, wherein the trait responsible for said stem structure is obtainable through introgression from a predecessor plant, which contains the genetic make-up of line 03P001, representative seed of which being deposited under accession number NCIMB 41228. A cauliflower plant exhibiting a stem structure as described above, wherein the trait responsible for said stem structure is introgressed form a predecessor plant, which contains the genetic make-up of line 03P001, representative seed of which being deposited under accession number NCIMB 41228.

The invention further provides:

Seed of any one of the cauliflower plants above.

Part of any one of the cauliflower plants above. In one embodiment, the part is a cell, pollen, an ovule, or a curd.

The invention further provides:

A method of producing a cauliflower curd comprising growing any one of the cauliflower plants above until a curd is produced and harvesting said curd. An agronomic method comprising growing any one of the cauliflower plants above until a curd ready for harvesting is produced; harvesting the curd. In one embodiment, the curd is harvested mechanically.

The invention further provides:

A method of harvesting a cauliflower curd comprising growing any one of the cauliflower plants above until a curd is produced and mechanically harvesting said curd. In one embodiment, a blade is used in said step of mechanically harvesting said curd.

The invention further provides:

A method of producing seed of a cauliflower plant comprising growing any one of the cauliflower plants above; allowing the cauliflower plant to self-pollinate; and harvesting seeds from the cauliflower plant.

The invention further provides:

A method of vegetatively propagating a cauliflower plant comprising collecting a tissue of any one of the cauliflower plants above; cultivating the tissue to obtain proliferated shoots; and rooting the proliferated shoots to obtain rooted plantlets.

The invention further provides:

A method for producing a plant comprising a long stem comprising crossing a broccoli plant and a cauliflower plant; obtaining a progeny plant from the cross; measuring the stem length or average internode length of the progeny plant; and selecting a plant comprising a long stem or long average internode length as described herein. In one embodiment, the method further comprises obtaining a dihaploid of the plant selected above.

A plant obtainable by any one of the methods above.

The invention further provides:

A method for producing a cauliflower plant comprising a long stem comprising crossing a cauliflower plant and a plant of line 03P001, representative seed of which being deposited under accession number NCIMB 41228; obtaining a progeny plant from the cross; measuring the stem length or average internode length of the progeny plant; and selecting a cauliflower plant with a long stem or long average internode length as described herein.

A cauliflower plant obtainable by any one of the methods above.

DEFINITIONS

Growing days: refers to the number of days from the date of transplanting of young plants into a field or a plot to the date when 50% of the plants in the field or plot reach maturity.

Maturity: a cauliflower plant has reached maturity when it has produced a curd that can be harvested and commercialized on the market (i.e. a marketable curd). Based on the certain market preference, the curd size can range from 15 cm to 30 cm in diameter.

Cycle: number of growing days under particular growing conditions. The length of the cycle is based on the genetics of a cauliflower plant and depends on the climatic conditions, in particular the night temperature, under which the plant is grown. The cycle is generally defined for specific climatic conditions, locations, sowing and transplanting times, or a combination thereof. Cauliflower plants, such as plants of inbred lines or hybrids, are for example grouped into short cycle (SC), medium cycle (MC), medium-long (MLC), long cycle (LC) and very long cycle (VLC).

Short cycle (SC): 60-70 growing days after transplanting, based on a January sowing and March transplanting in the conditions of North-Western Europe, for example Enkhuizen, The Netherlands. Typical plants of the SC are for example plants of variety Vinson (Seminis).

Medium cycle (MC): 60-72 growing days after transplanting, based on a May sowing and June transplanting in the conditions of North-Western Europe, for example Enkhuizen, The Netherlands. Typical plants of the MC are for example plants of variety Fremont (Seminis), Tetris (Syngenta Seeds) or Lecanu (Syngenta Seeds).

Medium long cycle (MLC): 73-90 growing days after transplanting, based on a May sowing and June transplanting in the conditions of North-Western Europe, for example Enkhuizen, The Netherlands. Typical plants of the MLC are for example plants of variety Amerigo (Syngenta Seeds).

Long cycle (LC): Typical plants of the LC are for example plants of variety Belot (Bejo). Very long cycle (VLC): Typical plants of the VLC are for example plants of variety Mayfair (Syngenta Seeds).

Loose foliage: Reduced amount of foliage due to either smaller number of leaves, reduced leaf size, or a combination thereof. Loose foliage is for example measured by the leaf volume index or total leaf weight. Loose foliage may also be measured by the number of internodes on the stem of a plant.

Persistent white curd: This trait prevents or slows down cauliflower curd turning yellow after exposure to sunlight. (see for example Dickson M. H. and Lee C. Y. Persitent white curd and other curd characters of the cauliflower. 1980 J. Amer. Soc. Hort. Sci. 105(4):533-535).

Trait: characteristic or phenotype. In the context of the present invention a trait is for example a long stem, long internodes, loose foliage or persistent white curd, as described herein. A trait may be inherited in a dominant or recessive manner, or in a partial or incomplete-dominant manner. A trait may be monogenic or polygenic, or may also result from the interaction of one or more genes with the environment.

Monogenic: determined by a single locus.

Polygenic: determined by more than one locus.

Dominant: results in a complete phenotypic manifestation at heterozygous or homozygous state.

Recessive: manifests itself only when present at homozygous state.

Partial or incomplete-dominance: when present at the heterozygous stage determines a phenotype that is intermediate to that of the homozygous stage or when the trait is absent.

Locus: region on a chromosome, which comprises a gene contributing to a trait.

Genetic linkage: association of characters in inheritance due to location of genes in proximity on the same chromosome. Measured by percent recombination between loci (centi-Morgan, cM).

Isogenic: plants, which are genetically identical, except that they may differ by the presence or absence of a gene, a locus conferring a trait or heterologous DNA sequence.

Marker assisted selection: refers to the process of selecting a desired trait or desired traits in a plant or plants by detecting one or more nucleic acids from the plant, where the nucleic acid is associated with the desired trait.

Dihaploid: doubling of haploid (single chromosome) status of the genome (e.g. through anther culture or microspore culture) giving a complete homozygous plant.

"Tester" plant: plant used to characterize genetically a trait in a plant to be tested. Typically, the plant to be tested is crossed with a "tester" plant and the segregation ratio of the trait in the progeny of the cross is scored.

Gene: Unit of inheritance. Genes are located at fixed loci in chromosomes and can exist in a series of alternative forms called alleles.

Allele: One of a pair or series of forms of a gene, which are alternative in inheritance because they are situated at the same locus in homologous chromosomes.

Homozygous: Having like alleles at one or more corresponding loci on homologous chromosomes.

Heterozygous: Having unlike alleles at one or more corresponding loci on homologous chromosomes.

As used herein, the term "plant" includes plant cells, plant protoplasts, plant cells of tissue culture from which cauliflower plants can be regenerated, plant calli, plant clumps, and plant cells that are intact in plants or parts of plants, such as pollen, flowers, seeds, curds, stalks, stumps, leaves and the like.

Plant Height: measured in centimeters (cm) from the soil line to the top of the leaves.

Stem length: measured in centimeters from the soil line to the bottom of the curd.

Average internode length: Stem length at maturity divided by the number of internodes on the stem.

Number of internodes: number of internodes on a stem at maturity.

Leaf Width: measured in centimeters at the widest part of the leaf blade midpoint of the plant including the petiole.

Leaf Length: length of leaf blade measured in centimeters from the midpoint of the plant including excluding the petiole.

Leaf volume index: leaf length in centimeters multiplied by leaf width in centimeter, divided by 1,000.

Total leaf weight: weight of all the leaves on a plant at the time of harvest of the curd.

Curd Diameter: measured at the widest diameter of the curd (from overhead) in centimeters.

Stem Diameter: measured in centimeters and is taken at a point just below the head.

Yield: the weight in grams for a harvested curd.

Color: means the color of the curd at maturity.

Field Holding Ability: means the ability of a plant to maintain good curd quality after the optimal harvest date.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

The instant application addresses the need to reduce the production costs for cauliflower, in particular harvesting costs, and to allow for more efficient harvesting of marketable cauliflower curds. While efforts have been made to develop machinery specifically adapted to the harvesting of cauliflower curds, the inventors of the instant application have addressed the above needs by an alternative strategy, comprising developing novel cauliflower plants. In particular, the inventors of the instant application have addressed the above needs by providing cauliflower plants with a special stem structure, especially cauliflower plants comprising a long stem. In one embodiment, the plants according to the instant invention are suitable for mechanical harvesting.

Cauliflower is a cool season plant tolerating temperatures as low as 4° C. and as high as 38° C. Cauliflower seeds are typically sown in trays filled with a soil mixture suitable for germination and raised to young plants. Generally, after about 4-6 weeks the young plants may transplanted to open fields. The plant density in a field may vary, but is typically around 3 plants per m$^2$. During the growing period plants are watered either by drip irrigation or by sprinklers. If climate is wet enough no irrigation is needed.

Cauliflower plants initially grow in a vegetative phase followed by a generative phase. Typically, the stems elongate during the vegetative phase, but their growth is generally reduced or even stops, as the generative phase begins. The generative phase is characterized by the development of the curd. Plants with early maturity (i.e. short cycle) have a short vegetative phase and need less growing days to produce a curd. They also tend to have short stems and produce fewer internodes. Plants with late maturity (i.e. longer cycle) have a longer vegetative phase and need more growing days. They also tend to produce longer stems, which is usually due to a higher number of internodes. Cauliflower plants need a certain "vernalization" (cool nights at approximately 16-18° C.) to induce curd formation. Absent such vernalization or curd induction, curd formation and consequently maturity is delayed. The duration of the vegetative phase depends on the climatic conditions. The warmer the mean temperature, the more likely it is for the plant to remain in the vegetative cycle, which increases the time needed to produce marketable curds. This typically results in more internodes and thus also more leaves. It is a general rule for cauliflower plants that the number of growing days increases when the night temperature is high. Therefore, the number of growing days defining the cycle of a cauliflower plant is generally defined for a crop sowed and transplanted at a specific time (expressed in week, month or season) in a particular climatic zone or location. The person skilled in the art would be able to recognize the cycle of a cauliflower plant.

Most cauliflower production is scheduled to accommodate specific temperature requirements by utilizing cultivars that are adapted to the variations of the seasons. Growers generally prefer plants with short to medium-long cycles, because they occupy the fields for less time, thus allowing better land use and limiting the risk of damage to the crop due to bad weather or disease. Also, in many climatic regions, plants with shorter maturity are desired, since they may otherwise be at risk of high temperatures in the summer or frost in the late fall or winter. However, plants with shorter cycles tend to produce shorter stems, which makes them particularly ill-suited for mechanical harvesting, and which make hand harvesting particularly strenuous. The instant invention is therefore particularly beneficial to plants of the shorter cycles, such as plants for the short to medium cycles, and, in one embodiment, a plant of the present invention is a plant of the short or medium cycles as defined herein.

Cauliflower curds are exclusively harvested by hand. Therefore, the development of new cauliflower types and cultivars has focused on traits facilitating hand harvesting. Such traits are for example end-product traits, such as curd quality and taste, and traits, which helped crop maintenances, for example resistance to diseases. An important area of research focused on developing cauliflower types with leaf structures covering the curd to avoid the need to protect curd by hand during the harvest, and generally also characterized by heavy foliage. Another important area of research was to provide an upright plant habit to increase the plant number per acreage.

By contrast, the features of long stem and long internodes are undesirable for cauliflower curds harvested by hand, because they make the plants more vulnerable to lodging, which can cause rotting on the curd or on the surrounding leaves. Lodged plants also make hand harvest more difficult. The traits of long stem and long internodes were therefore systematically eliminated from the cauliflower germplasm pool.

Accordingly, the inventors of the present invention have evaluated other sources for the traits of long stem and long internodes, in particular other *brassica* species. In one embodiment, the traits of long stem and long internodes were obtained from another *brassica* species, in one embodiment from broccoli (*Brassica oleracea* L. Italica). However, crosses between species can have unexpected, unfavorable consequences, in particular when the plant's architecture is modified. Also, the cauliflower curd is a very delicate structure with a particular taste, consistency and appearance, and other *brassica* species have numerous traits, which are undesirable in a cauliflower curd. In particular, the head type and the green color of the head of broccoli plants are undesired in cauliflower. Accordingly, in one embodiment, the trait of long stem and long internodes according to the instant invention was obtained from broccoli and successfully transferred to cauliflower, while surprisingly avoiding other undesired broccoli traits, and in one embodiment, a cauliflower plant of the instant invention is a cauliflower plant having commercially desirable attributes, such as capable of producing a marketable curd.

In one embodiment, a cauliflower plant was crossed to a broccoli plant. The resulting F1 progeny was self-pollinated and selected for long stem and long internodes and for the best possible cauliflower curd. Selected F2 progenies were again self-pollinated and selected for long stem and long internodes and for the best possible cauliflower curd. In some case, self-pollination and selection was repeated. The best F2 or F3 plants were subjected to the dihaploid technique for line fixation in order to get the highest possible uniformity of plants of a particular line. F1 and subsequent generations could also be back-crossed with cauliflower plants having desired characteristics to improve curd quality.

Accordingly, the instant application also provides methods of producing a plant of the present invention comprising crossing a cauliflower plant with a broccoli plant and selecting for plants comprising a long stem and characteristics of a cauliflower curd. In one embodiment, the present invention discloses a method of increasing the stem length of a cauliflower plant, for example comprising the steps disclosed above. The present invention also discloses a cauliflower plant obtainable by the method above, wherein the plant is capable of producing one or more traits as described herein.

The instant application also provides methods of producing a plant of the present invention comprising crossing a cauliflower plant with a broccoli plant and selecting for plants comprising long internodes and characteristics of a cauliflower curd. In one embodiment, the present invention discloses a method of increasing the stem length of a cauliflower plant, for example comprising the steps disclosed above. In one embodiment, the present invention discloses a method of increasing the average internode length of the stem of a cauliflower plant, for example comprising the steps disclosed above. The present invention also discloses a cauliflower plant obtainable by the method above, wherein the plant is capable of producing one or more traits as described herein.

The instant application also provides methods of producing a plant of the present invention comprising crossing a cauliflower plant with a broccoli plant and selecting for plants comprising a long stem and long internodes and characteristics of a cauliflower curd. In one embodiment, the present invention discloses a method of increasing the stem length of a cauliflower plant, for example comprising the steps disclosed above. The present invention also discloses a cauliflower plant obtainable by the method above, wherein the plant is capable of producing one or more traits as described herein.

In one embodiment, the present invention provides novel cauliflower plants with a special stem structure. In one embodiment, the novel cauliflower plants provided herein comprise a long stem. In one embodiment, a cauliflower plant of the present invention is a plant of the short cycle or of the medium cycle and comprises at maturity a stem length of at least about 22.5 cm, optionally at least about 25 cm, in particular when the plant is grown under conditions representative for a continental climate, e.g. in Ocsa, Hungary, and planted during the 3$^{rd}$ week of May and transplanted during the 3$^{rd}$ week of June, or when the plant is grown under conditions representative for a Mediterranean climate, e.g. in Murcia, Spain, and planted during the 1$^{st}$ week of August and transplanted during the 1st week of September (see e.g. Examples 3 and 4 below). In one aspect, the stem length is about 22.5 cm to about 35 cm, optionally about 25 cm to about 35 cm, in particular when grown under the conditions above.

Alternatively, a cauliflower plant of the present invention is a plant of the short cycle or of the medium cycle and comprises at maturity a stem length of at least about 30 cm, optionally at least 32.5 cm, when grown under conditions representative for a continental climate, e.g. in Ocsa, Hungary, and planted during the 4$^{th}$ week of May and transplanted during the 5th week of June (see e.g. Example 5 below). In one aspect, the stem length is about 30 cm to about 45 cm, optionally about 32.5 cm to about 42.5 cm, when grown under the conditions above.

In one embodiment, a cauliflower plant of the present invention comprises at maturity a stem length of at least 85% of the length of the stem of a plant of line 03P001 (the male parent of cauliflower hybrid CFL5752), representative seeds of which is deposited with NCIMB under accession number NCIMB 41228. In one aspect, a cauliflower plant of the present invention comprises at maturity a stem length of at least 90% of the length of the stem of a plant of line 03P001. In one embodiment, a cauliflower plant of the present invention comprises at maturity a stem length of about 85% to about 130%, optionally about 85% to about 120%, about 85% to about 115% or about 85% to about 110%, of the length of the stem of a plant of line 03P001.

In one embodiment, the stem of a plant of the present invention is longer than that of currently existing cauliflower plants having commercially desirable attributes, such as capable of producing a marketable curd, and requiring approximately the same number of growing days to reach maturity, for example at least about 10% longer, at least about 15% longer, or at least about 20% longer. Alternatively, the stem of a plant of the present invention is longer than that of currently existing cauliflower plants in the same cycle having commercially desirable attributes, such as capable of producing a marketable curd, for example at least about 10% longer, at least about 15% longer, or at least about 20% longer. In one aspect, the stem of a plant of the present invention is about 110% to about 200% the length of the stem of currently existing cauliflower plants having commercially desirable attributes, such as capable of producing a marketable curd, and requiring approximately the same number of growing days to reach maturity, optionally about 110% to about 180%. In one aspect, the stem of a plant of the present invention is about 110% to about 200% the length of the stem of currently existing cauliflower plants in the same cycle having commercially desirable attributes, such as capable of producing a marketable curd, optionally about 110% to about 180%.

In one embodiment, such a currently existing cauliflower plants is a typical plants in the cycle. In one embodiment such a currently existing cauliflower plants is a plant of variety Fremont or, alternatively, of variety Lecanu and the stem of a plant of the present invention is longer than that of a plant of variety Fremont or variety Lecanu. In one aspect, the stem of a plant of the present invention is longer than the stem of a plant of variety Fremont or variety Lecanu, in for example at least about 10% longer, at least about 15% longer, or at least about 20% longer. In one aspect, the stem of a plant of the present invention is about 110% to about 200% the length of the stem of variety Fremont or variety Lecanu, optionally about 110% to about 180%.

In one embodiment, the stem of a plant of the present invention reaches a stem length suitable for mechanical harvesting sooner than a cauliflower plant of a longer cycle.

In one embodiment, the stem of a plant of the instant invention comprises long internodes. In one embodiment, the average internode length of the stem of a plant of the present invention is at least 1.25 cm long (see e.g. Example 5 below). In one aspect, the average internode length of the stem of a plant of the present invention is at least 1.25 cm long when grown under conditions representative for a continental climate, e.g. in Ocsa, Hungary, and for example planted during the 4$^{th}$ week of May and transplanted during the 5th week of June. Optionally, the average internode length of the stem of a plant of the present invention is at least 1.30 cm long, at least 1.35 cm long, or 1.40 cm long, especially when grown under the conditions above. Alternatively, the average internode length of the stem of a plant of the present invention is 1.25 cm to 2.00 cm, especially when grown under the conditions above.

In one embodiment, the average internode length of the stem of a plant of the present invention is at least 80% of the average internode length of the stem of a plant of line 03P001. In one aspect, the average internode length of the stem of a plant of the present invention is at least 85%, optionally at least 90%, of the average internode length of the stem of a plant of line 03P001. In one aspect, the average internode length of the stem of a plant of the present invention is 80% to 140% of the average internode length of the stem of a plant of line 03P001. Optionally, the average internode length of the stem of a plant of the present invention is 80% to 130% or 80% to 120% of the average internode length of the stem of a plant of line 03P001.

In one embodiment, the average internode length of the stem of a plant of the present invention is longer than that of currently existing cauliflower plants having commercially desirable attributes, such as capable of producing a marketable curd. In one aspect, the average internode length of the stem of a plant of the present invention is longer than that of currently existing cauliflower plants having commercially desirable attributes, such as capable of producing a marketable curd and requiring approximately the same number of growing days to reach maturity. Alternatively, the average internode length of the stem of a plant of the present invention is longer than that of currently existing cauliflower plants in the same cycle having commercially desirable attributes, such as capable of producing a marketable curd.

In one embodiment, the average internode length of the stem of a plant of the present invention is at least 20% longer than the average internode length of the stem of a plant of variety Lecanu or, alternatively, of variety Fremont. Optionally, the average internode length of the stem of a plant of the present invention is at least 25% longer or at least 30% longer than the average internode length of the stem of a plant of variety Lecanu or variety Fremont. Alternatively, the average internode length of the stem of a plant of the present invention is 20% to 80% longer than the average internode length of the stem of a plant of variety Lecanu or variety Fremont.

Typically, cauliflower curds are harvested when they are still tight and compact, and surrounded by inner leaves. The inner leaves protect the curd during the harvest by hand. Inner leaves surrounding the curd tend to be associated with large leaves or a large numbers of leaves, or both. This can cause jams in harvesting machines, and slow down mechanical harvesting of the curds. Accordingly, in one embodiment, a plant of the instant invention further comprises a trait of loose foliage. In one aspect, the trait of loose foliage is obtained from a broccoli plant.

In one embodiment, the total leaf weight of a plant of the instant invention is lower than the total leaf weight of currently existing cauliflower plants having commercially desirable attributes, such as capable of producing a marketable curd. In one aspect, the total leaf weight of a plant of the instant invention is lower than the total leaf weight of currently existing cauliflower plants having commercially desirable attributes, such as capable of producing a marketable curd and requiring approximately the same number of growing days to reach maturity. Alternatively, the total leaf weight of a plant of the instant invention is lower than the total leaf weight of currently existing cauliflower plants in the same cycle having commercially desirable attributes, such as capable of producing a marketable curd.

In one embodiment, the total leaf weight of a plant of the present invention is less than 150% of the total leaf weight of a plant of line 03P001 (see e.g. Example 5 below). Optionally, the total leaf weight of a plant of the present invention is less than 140%, less than 130%, less than 120 or less than 110%, of the total leaf weight of a plant of line 03P001. In one aspect, the total leaf weight of a plant of the present invention is 80% to 150% of the total leaf weight of a plant of line 03P001.

In one embodiment, the leaf volume index of a plant of the instant invention is smaller than the leaf volume index of currently existing cauliflower plants having commercially desirable attributes, such as capable of producing a marketable curd. In one aspect, the leaf volume index of a plant of the instant invention is smaller than the leaf volume index of currently existing cauliflower plants having commercially desirable attributes, such as capable of producing a marketable curd and requiring approximately the same number of growing days to reach maturity. Alternatively, the leaf volume index of a plant of the instant invention is smaller than the leaf volume index of currently existing cauliflower plants in the same cycle having commercially desirable attributes, such as capable of producing a marketable curd.

In one embodiment, the leaf volume index of a plant of the present invention is less than 130% of the leaf volume index of a plant of line 03P001 (see Example 5 below). Optionally, the leaf volume index of a plant of the present invention is less than 125%, less than 120%, or less than 110%, of the leaf volume index of a plant of line 03P001. In one aspect, the leaf volume index of a plant of the present invention is 80% to 130% of the leaf volume index of a plant of line 03P001.

In one embodiment, the length of the stem of a plant of the present invention is longer because of longer internodes, while the number of internodes on the stem, and thus the number of leaves of the plants, remains approximately the same or is reduced, when compared with currently existing cauliflower plants having commercially desirable attributes, such as capable of producing a marketable curd and requiring approximately the same number of growing days to reach maturity or in the same cycle. The feature of longer internodes thus offers the advantage of providing longer stems while maintaining a low number of leaves on the stem or reducing the number of leaves on the stem.

Accordingly, in one embodiment, a plant of the instant invention comprises a trait of long stems or long internodes as described herein, and further comprises less than 120% of the number of internodes of a plant of line 03P001. Optionally, a plant of the present invention comprises less than 115% or less that 110% of the number of internodes of a plant of line 03P001. In one aspect, plant of the present invention comprises 80% to 120% the number of internodes of a plant of line 03P001.

In one embodiment, a plant of the present invention comprises 18 internodes to 26 internodes. Alternatively, the plant comprises 19 internodes to 25 internodes, or 20 internodes to 24 internodes, for example when the plants are grown under conditions representative for a continental climate, e.g. in Ocsa, Hungary, and for example planted during the $4^{th}$ week of May and transplanted during the 5th week of June.

In one embodiment, a plant of the instant invention further comprises a trait of persistent white curd. A persistent white curd has the advantage of preventing or slowing down the cauliflower curd turning yellow after exposure to sunlight. The trait of persistent white curd is for example described in Dickson and Lee (1980) Journal-of-the-American-Society-for-Horticultural-Science, 105(4): 533-535 or in Dickson (1985) HortScience, 0(5): 957. In one embodiment, the trait of persistent white is obtained from PI 183214, also described in the above references. Example 6 below describes the transfer of the persistent white trait to a cauliflower plant of the instant invention.

Cauliflower plants with a trait of loose foliage produce curds, which are less protected by inner leaves. Such curds are therefore more exposed to sunlight. Accordingly, in one embodiment, the trait of persistent white is combined with the trait of loose foliage, and in one embodiment, a plant of the instant invention further comprises a trait of loose foliage and a trait of persistent white curd. Such cauliflower plants have the advantage of producing fewer or smaller leaves, and thus prevent jamming of mechanical harvesters, while preventing or slowing down the cauliflower curd turning yellow after exposure to sunlight.

When plants are compared in the context of the instant application, for example when a trait is compared between a plant of the present invention and a plant of line 03P001 or a plant of variety Fremont or variety Lecanu, the plants are typically grown under the same conditions, for example in the same experiment. In one aspect, the plants are grown under the conditions set forth in the examples below, for example under conditions representative for a continental climate, e.g. in Ocsa, Hungary, and for example planted during the $4^{th}$ week of May and transplanted during the 5th week of June.

In one embodiment, a plant of the present invention comprises any combination the traits of long stem, long internodes, loose foliage, number of internodes, total leaf weight, leaf volume index and persistent white curd, and short or medium cycle and uniformity, as described herein. In one embodiment, a plant of the present invention comprises a long stem, loose foliage and persistent white curd, as described herein. In one embodiment, such plant is of the short cycle or medium cycle.

In one embodiment, a plant of the present invention comprises a long stem and long internodes, as described herein. In one aspect, the plant comprises a long stem, long internodes and number of internodes, as described herein. In another aspect, the plant comprises a long stem, long internodes and low total leaf weight, as described herein. Alternatively, the plant comprises a long stem, long internodes and small leaf volume index, as described herein. Optionally, the plant comprises a long stem, long internodes, number of internodes, low total leaf weight and small leaf volume index, as described herein. In one embodiment, the plant is of the short cycle or medium cycle.

In one embodiment, a plant of the present invention comprises a long stem and low total leaf weight, as described herein. In one aspect, the plant comprises a long stem, long internodes and number of internodes, as described herein. In another aspect, the plant comprises a long stem and small leaf volume index, as described herein. Alternatively, the plant comprises a long stem, number of internodes, low total leaf weight and small leaf volume index, as described herein. In one embodiment, the plant is of the short cycle or medium cycle.

In one embodiment, a plant of the present invention comprises long internodes and low total leaf weight, as described herein. In one aspect, the plant comprises long internodes and number of internodes, as described herein. In another aspect, the plant comprises long internodes and small leaf volume index, as described herein. Alternatively, the plant comprises long internodes, number of internodes, low total leaf weight and small leaf volume index, as described herein. In one embodiment, the plant is of the short cycle or medium cycle.

In one embodiment, plants of the instant invention of a line or hybrid have a high level of uniformity in plant habit. In one embodiment, plants of the instant invention of a line or hybrid have a high level of uniformity in growing days. In one embodiment, plants of the instant invention of a line or hybrid have a high level of uniformity in plant habit and growing days. These features facilitate the use of fully or partly automatic mechanical harvesters. High level of uniformity in plant type is desirable for high through-put machine harvest to avoid losses due to the different plant shapes, while uniformity in maturation limits the number of passes over the field required, further decreasing the cost of the harvest. This results in a high proportion of marketable products. High uniformity makes frequent adaptation of the harvester, in extreme case one-by-one examination of plants, unnecessary during the harvest process and allows use of a machine at its highest capacity. In one embodiment, high level of uniformity is achieved by the application of double haploid technique on the plants of the instant invention (see e.g. Bagga, S. et al. (1982). Comparison of in vitro plant formation from somatic tissues and pollen grains in Brassica oleracea var. botrytis. Phytomorphology 32, p 152-156; Ockendon, D. J. (1988). The ploidy of plants obtained from anther culture of cauliflowers (Brassica oleracea var. botrytis). Ann. appl. Biol. 113, p 319-325). Accordingly, in one embodiment, a plant of the present invention is a dihaploid or the descendent of a dihaploid plant, for example a hybrid having a dihaploid as parent line.

Based on the description of the present invention, the skilled person is able to recognize a cauliflower plant of the instant invention under various growing conditions. Accordingly, the present invention also further discloses a method of identifying a cauliflower plant of the instant invention comprising growing a cauliflower plant until said plant reaches maturity and measuring the length of the stem, length of internodes, total leaf weight or leaf volume index of said plant. Based on the description of the present invention, the skilled person is also able to transfer a trait of cauliflowers plant of the present invention to other cauliflower plants, in particular to any type of cauliflower types using breeding techniques well-known in the art. Cauliflower types include for example white cauliflower, green cauliflower, purple cauliflower and orange cauliflower, or cauliflower of the Romano type. Based on the description of the present invention, the skilled person is also able to transfer a trait of cauliflowers plant of the present invention to cauliflower plants of other cycles using breeding techniques well-known in the art.

The values for stem length, average internode length, number of internodes, total leaf weight, leaf length, leaf width and leaf volume index disclosed in the instant application are averages based the measurement of these characteristics for a representative number of plants, unless otherwise stated.

Representative cauliflower plants according to the instant invention are described in the Examples below. For example, cauliflower hybrid CFL5752 of the present invention (medium cycle) was grown in the same trial as variety Fremont (medium cycle), variety Lecanu (medium cycle) and variety Amerigo (medium-long cycle). The stem length was measured at maturity and is reported in Table 1. Generally, the stem length is reported herein as an average, typically calculated from the measurement of 15 to 20 stems of plants of a line or hybrid. It is understood that measurements in independent experiments may vary because of different environmental conditions.

Seeds of line 03P001, a representative line according to the instant invention, were deposited under the Budapest treaty with NCIMB, Ltd., Aberdeen, Scotland, UK, on Jun. 28, 2004 under accession number NCIMB 41228. Line 03P001 is the male parent of cauliflower hybrid CFL5752 and is also further described in the Examples herein.

In one embodiment, a plant of the present invention is obtainable from a plant of line 03P001, seeds of which was deposited under accession no. NCIMB 41228, or from a progeny or ancestor of said line, which comprises long stems according to the instant invention.

In one embodiment, the present invention further discloses a method of transferring one or more traits according to the present invention, for example long stems, to a cauliflower plant lacking said trait(s) comprising a) obtaining a plant comprising said trait(s); b) crossing it to a plant lacking said trait(s); c) obtaining plants of the cross of step b); d) selecting a plant of step c) which is capable of producing one or more traits according to the present invention. Optionally, the method further comprises e) back-crossing a plant resulting from step d) with a cauliflower plant, and f) selecting for a cauliflower plant, which is capable of producing one or more traits according to the present invention. In one aspect, the method further comprises obtaining an inbred cauliflower plant, which is capable of producing one or more traits according to the present invention, and, in another aspect, the method further comprises crossing said inbred cauliflower plant to another cauliflower plant to produce a hybrid cauliflower plant, which is capable of producing one or more traits according to the present invention. In one embodiment, the plant of step a) comprising said trait(s) is a plant of line 03P001 or a progeny or ancestor of said plant. In one embodiment, the plant of step a) is a broccoli plant.

In one embodiment, the present invention discloses a cauliflower plant obtainable by any one of the methods above, wherein the plant is capable of producing one or more trait as described herein.

In one embodiment, the present invention discloses a method of producing a plant comprising one or more traits according to the present invention, for example long stems, to a cauliflower plant lacking said trait(s) comprising a) obtaining a plant comprising said trait(s); b) crossing it to a plant lacking said trait(s); c) obtaining plants of the cross of step b); d) selecting a plant of step c) which is capable of producing one or more traits according to the present invention. Optionally, the method further comprises e) back-crossing a plant resulting from step d) with a cauliflower plant, and f) selecting for a cauliflower plant, which is capable of producing one or more traits according to the present invention. In one aspect, the method further comprises obtaining an inbred cauliflower plant, which is capable of producing one or more traits according to the present invention, and, in another aspect, the method further comprises crossing said inbred cauliflower plant to another cauliflower plant to produce a hybrid cauliflower plant, which is capable of producing one or more traits according to the present invention. In one embodiment, the plant of step a) comprising said trait(s) is a plant of line 03P001 or a progeny or ancestor of said plant. In one embodiment, the plant of step a) is a broccoli plant.

In one embodiment, the present invention discloses a cauliflower plant obtainable by any one of the methods above, wherein the plant is capable of producing one or more traits as described herein.

Commercial cauliflowers are generally hybrids produced from the cross of two parental lines (inbreds). The development of hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5; etc.

A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

Cauliflower plants can be easily cross-pollinated. A trait is readily transferred from one cauliflower plant to another cauliflower plant, including cauliflower plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait. The progeny of this cross is then mated back to the recurrent parent followed by selection in the resultant progeny for the trait. After three, preferably four, more preferably five or more generations of backcrosses with the recurrent parent with selection for the trait, the progeny is heterozygous for the locus harboring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross.

In one embodiment, a cauliflower plant of the present invention is male sterile. Male sterility is of value in *B. oleracea* hybrid seed breeding because normal flowers are self-pollinating. Male sterile lines do not produce viable pollen and cannot self-pollinate. By eliminating the pollen of one parental variety in a cross, a plant breeder is assured of obtaining hybrid seed of uniform quality. A particularly advantageous male sterility system is cytoplasmic male sterility (CMS). An example of such CMS in *Brassica* is the Ogura CMS originally found in radish (see for example Ogura (1968) Mem. Fac. Agric. Kagoshima Univ. 6: 39-78; Makaroff (1989) Journal of Biol. Chem. 264: 11706-11713; U.S. Pat. No. 5,254,802). Therefore, the present invention discloses a male sterile, in particular CMS, cauliflower plant, including seeds and materials of said plants and the progeny thereof. In one embodiment, a plant of the instant invention is a maintainer plant.

The male fertility of male sterile plants can be restored by methods well-known in the art. The male fertility of CMS plants, in particular CMS *B. oleracea* plants, is preferably restored by cell fusion. For this, cells of a CMS plant are fused to cells of a male fertile plant to replace the nucleus of the fertile plant by the nucleus of sterile plant in the fertile cytoplasmic background, and restore fertility. Cell fusion techniques are well-known in the art and are for example described in Sigareva and Earle (1997) Theor. Appl. Genet. 94: 213-320. Using such techniques, male fertile plants are regenerated, and allowed to self-pollinate or crossed to another plant.

In one embodiment, a plant of the present invention is an inbred, a hybrid, or a dihaploid, for example produced by pedigree breeding or by recurrent selection breeding. In one embodiment, a plant of the present invention has commercially acceptable agronomic characteristics.

In one embodiment, the present invention discloses a method of producing seed of a cauliflower plant of the present invention comprising: a) growing a plant of the present invention; b) allowing said plant to self-pollinate; c) harvesting seeds from said plant.

Cauliflower plants can also be propagated vegetatively using methods well-known in the art, for example in-vitro plant tissue culture, rooting side shoot or protoplast fusion. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets; d) growing plants from said rooted plantlets; and harvesting seeds from said plants.

Cauliflower plants of the present invention can also be transformed genetically with a gene of interest, using techniques well known in the art. Accordingly, the present invention also further disclose a cauliflower plant according to the instant invention further such a gene of interest.

In one embodiment, the present application discloses methods of producing a cauliflower curd comprising growing a plant of the invention until a curd is produced and harvesting the curd. In one aspect, the curd is harvested mechanically.

In one embodiment, the present application discloses methods of harvesting a cauliflower curd comprising growing a plant of the invention until a curd is produced and mechanically harvesting said curd. In one aspect, a blade is used in the step of mechanically harvesting the curd. In one embodiment, the curd is loaded on a belt.

All references cited herein are incorporated by reference in the instant application in their entireties. The following examples are intended to provide illustrations of the application of the present invention. The following examples are not intended to completely define or otherwise limit the scope of the invention.

EXAMPLES

Example 1

Development of Line 03P001 and of Hybrid CFL5752

Plants of cauliflower line B66-1, a Syngenta breeding line, were crossed to plants of a Syngenta broccoli breeding line. The resulting F1 progeny was self-pollinated and selected for long stem and internode, and for the best possible cauliflower curd. Selected F2 progenies were again self-pollinated and selected for long stem and internode and for the best possible cauliflower curd. These steps were repeated for selected F3 progenies.

Selected F3 progenies were subjected to double haploid culture using a standard protocol. The resulting dihaploid lines were again selected for long stem and internode and for the best possible cauliflower curd. Line 03P001 was identified.

About 20 lines were crossed with the female parent of hybrid commercial hybrid Amerigo (Syngenta Seeds) to obtain F1 hybrids. In particular, line 03P001 was crossed with the female parent of Amerigo to obtain hybrid CFL5752.

Example 2

Characteristics of Hybrid CFL5752

Hybrid CFL 5752 typically reaches maturity at approximately 63 days after transplanting, when seeds are sown in January (week 3) and young plants transplanted in week 13, under growing conditions in Enkhuizen, The Netherlands.

Example 3

Measurements of Stem Length

The stem length of cauliflower hybrid CFL5752 was compared to that of varieties Fremont and Amerigo, and to that of the female parent of Amerigo and CFL5752. Variety Fremont is a medium cycle variety of Seminis. Amerigo is a medium-long cycle variety of Syngenta. Fremont and Amerigo were used standard varieties for the medium cycle and the medium-long cycle, respectively.

Experiment 1 was conducted in Ocsa, Hungary, under conditions representative for a continental climate. In Experiment 1, seeds were sown on May 18, 2004 and transplanted on Jun. 16, 2004. Plants were grown in open fields watered by sprinklers, with a plant density of approximately 3 plant/m² (60 cm row distance, 55 cm plant distance within a row). The average maximal temperature during the growing period was: June 24.1° C.; July 26.6° C.; August 26.9° C. The average minimum temperature during the growing period was: June 13.8° C.; July 16.7° C.; August 15.4° C.

Experiment 2 was conducted in Murcia, Spain, under conditions representative for a mediteranean climate. In Experiment 2, seeds were sown on Aug. 2, 2004 and transplanted on Sep. 3, 2004 Plants were grown in open field with drip irrigation, with a plant density of approximately 3.3 plant/m² (1 m row distance, 30 cm plant distance within a row). The average maximal temperature during the growing period was: September 27.0° C.; October 24.2° C.; November 17.9° C.; December 15.7° C. The average minimum temperature during the growing period was: September 18.5° C.; October 13.3° C.; November 7.3° C.; December 9.0° C.

Plants were grown until the curds of 50% of the plants of a certain plot were ready to be harvested. This time point was calculated from the date young plants were transplanted and is reported in the Tables as the number of growing days in the field. At this time point, plants having achieved an optimal harvest time were selected and measurements of the length of their stems was carried out. The number of growing days in the second trial is higher than in the first trial. This is because the night temperature was higher in Murcia (Exp. 2) than in Ocsa (Exp. 1). Table 1 shows the number of stems measured, the average stem length and the standard deviation.

Table 2 shows the results for individual plots in Experiment 2, leading to the averages shown in Table 1.

TABLE 1

| | Exp. 1 (2004) | | Exp. 2 (2004) | | Harvest |
|---|---|---|---|---|---|
| | stem length (cm) | days after transplanting | stem length (cm) | days after transplanting | time (week number) |
| CFL5752 | | | | | 47-50 |
| Avg | 26.3 | 56 | 28.3 | 84.6 | |
| Std Dev | 3.0 | | 2.7 | | |
| No. of plants | 27 | | 94 | | |
| Fremont | | | | | 47-49 |
| Avg | 19.8 | 56 | 18.9 | 80.4 | |
| Std Dev | 1.9 | | 2.5 | | |
| No. of plants | 40 | | 78 | | |
| Amerigo | | | | | 51-52 |
| Avg | 28.3 | 70 | 28.0 | 104.4 | |
| Std Dev | 2.1 | | 1.5 | | |
| No. of plants | 40 | | 87 | | |
| Female of Amerigo | | | | | 47-50 |
| Avg | 28.9 | 61 | 26.7 | 89 | |
| Std Dev | 2.9 | | 3.1 | | |
| No. of plants | 18 | | 19 | | |

TABLE 2

Individual plots in Exp. 2: stem length (cm)

| | | | | | | days after transplanting, avg. over plots |
|---|---|---|---|---|---|---|
| CFL5752 | 2005/2 | 2005/32 | 2005/48 | 2005/69 | 2005/104 | 84.6 |
| Avg | 26.1 | 30.3 | 28.6 | 28.8 | 27.5 | |
| Std Dev | 2 | 1.9 | 3.4 | 2.2 | 2.1 | |

TABLE 2-continued

Individual plots in Exp. 2: stem length (cm)

|  |  |  |  |  | days after transplanting, avg. over plots |
|---|---|---|---|---|---|---|
| No of plants | 18 | 19 | 20 | 17 | 20 |  |
| Fremont | 2005/3 | 2005/33 | 2005/49 | 2005/70 |  | 80.4 |
| Avg | 19.0 | 19.5 | 17.4 | 19.3 |  |  |
| Std Dev | 2.8 | 1.7 | 2.1 | 3.1 |  |  |
| No of plants | 20 | 20 | 18 | 20 |  |  |
| Amerigo | 2005/1 | 2005/31 | 2005/47 | 2005/68 | 2005/103 | 104.4 |
| Avg | 26.3 | 28.9 | 27.8 | 28.3 | 28.6 |  |
| Std Dev | 0.8 | 1.2 | 1.6 | 1.4 | 1.0 |  |
| No of plants | 17 | 18 | 18 | 17 | 17 |  |
| Female of Amerigo | 2005/50 |  |  |  |  | 89 |
| Avg | 26.7 |  |  |  |  |  |
| Std Dev | 3.1 |  |  |  |  |  |
| No of plants | 19 |  |  |  |  |  |

Example 4

Measurements of Stem Length

A number of representative cauliflower plants of the instant invention are described below. Plants were grown under the same conditions are in Experiment 2 in Example 3 above. The stem length was measured and shown in Table 3 below.

Female of Amerijo: Medium vigour, erected plant habit, medium stem length and internode length. Plant is open, curd shape is flat, curd density is medium. Medium-long cycle.

Male of CFL5752 (line 03P001): Medium vigour, erected plant habit, long stem and internodes. Plant is open, curd shape is domic and free of harriness, curd density is good. Medium cycle.

Handcross 14: Vigorous hybrid plant with long stem and long internodes. Plant is open, curd shape is domic, smooth and free of harriness. Curd density is medium. Medium cycle.

Handcross 17: Medium vigour, erected hybrid plant habit, long stem and internodes. Plant is open, curd shape is domic and free of harriness. Curd density is medium. Medium cycle.

Handcross 64: Hybrid plant with medium vigour, long stem and internodes. Plant is open, curd shape is domic and free of harriness. Curd density is medium. Medium cycle.

F6 line: Vigorous plant with long stem and long internodes and open bottom closure.

Plant is open, curd shape is flat, smooth and free from harriness. Curd density is modest. Medium cycle.

DH line 122: Dihaploid with medium vigour, long stem and internodes and open bottom closure. Plant is open, curd shape is flat and free of harriness. Curd density is modest. Medium cycle.

DH line 123: Dihaploid with medium vigour, long stem and internode. Plant is open, curd shape is flat and free of harriness. Curd density is modest. Medium cycle.

TABLE 3

|  | stem length (cm) | days after transplanting | Harvest time (week number) |  | stem length (cm) | days after transplanting | Harvest time (week number) |
|---|---|---|---|---|---|---|---|
| Female of Amerigo | 2005/50 | 89 | 47-50 | DH line (male of CFL5752) | 2005/54 | 89 | 48-50 |
| Avg | 26.7 |  |  | Avg | 30.2 |  |  |
| Std Dev | 3.1 |  |  | Std Dev | 1.6 |  |  |
| No. of plants | 19 |  |  | No. of plants | 19 |  |  |
| Handcross 14 | 2005/14 | 78 | 47-50 | Handcross 17 | 2005/17 | 77 | 47-49 |
| Avg | 30.3 |  |  | Avg | 30.4 |  |  |
| Std Dev | 2.4 |  |  | Std Dev | 2.5 |  |  |
| No. of plants | 16 |  |  | No. of plants | 18 |  |  |
| Handcross 64 | 2005/64 | 78 | 47-49 | line F6 | 2005/90 | 87 | 47-50 |
| Avg | 28.6 |  |  | Avg | 28.0 |  |  |
| Std Dev | 2.9 |  |  | Std Dev | 3.5 |  |  |
| No. of plants | 20 |  |  | No. of plants | 16 |  |  |
| DH line 122 | 2005/122 | 71 | 47-48 | DH line 123 | 2005/123 | 75 | 47-48 |
| Avg | 32.7 |  |  | Avg | 31.0 |  |  |
| Std Dev | 2.1 |  |  | Std Dev | 1.8 |  |  |
| No. of plants | 20 |  |  | No. of plants | 20 |  |  |

Example 5

Comparative Measurements

The stem length, number of leaves, average internode length, total leaf weight, leaf length, leaf width and leaf volume of a number of representative plants of the present invention are described in Table 4. Variety Amerigo was used as a standard variety for the medium-long cycle. Varieties Fremont and Lecanu were used a standard varieties for the medium cycle.

The experiment was conducted in Ocsa, Hungary, under conditions representative for a continental climate. Seeds were sown on May 27, 2005 and transplanted on Jun. 28, 2005. Plants were grown in open fields watered by sprinklers, with a plant density of approximately 3 plant/m$^2$ (60 cm row distance, 55 cm plant distance within a row). The average maximal temperature during the growing period was: July 23.6° C.; August 26.9° C.; September 24.6° C. The average minimum temperature during the growing period was: July 15.7° C.; August 15.4° C.; September 12.3° C.

Plants were grown until the curds of 50% of the plants of a certain plot were ready to be harvested. This time point was calculated from the date young plants were transplanted and is reported in the Tables as the number of growing days in the field (days after transplanting). At this time point, plants having achieved an optimal harvest time were selected and measurements were carried out when individual plants were ready for harvest.

Table 4 shows the number of plant for each entry and the average and standard deviation for each measurement. For the measurements of leaf length and width, 3 fully developed leaves were measured for each individual plant.

The number of growing days in the second trial in Ocsa was higher than in the first trial at this location (Experiment 1, Table 1). The second trial was planted two weeks later than the first one. The temperature was warmer when the plants needed vernalization for curd induction. This caused approximately two weeks delay in maturity and had an effect on stem length, leading to longer stems in the second experiment.

TABLE 4

|  | Stem length (cm) | Number of internodes | Internode length (cm) | Total leaf weight (kg) | Leaf length (cm) | Leaf width (cm) | Leaf volume index = length × width/1000 | Maturity (days after planting) |
|---|---|---|---|---|---|---|---|---|
| Amerigo |  |  |  |  |  |  |  | 83.1 |
| Average | 34.8 | 29.9 | 1.16 | 1.625 | 54.07 | 23.45 | 1.27 |  |
| Std Dev | 2.6 | 1.8 | 0.13 | 0.273 | 4.23 | 2.42 | 0.19 |  |
| No. plants: 14 |  |  |  |  |  |  |  |  |
| CFL5752 |  |  |  |  |  |  |  | 73.4 |
| Average | 35.2 | 23.4 | 1.50 | 1.154 | 55.44 | 24.19 | 1.34 |  |
| Std Dev | 3.3 | 3.2 | 0.26 | 0.273 | 3.71 | 2.40 | 0.21 |  |
| No. plants: 27 |  |  |  |  |  |  |  |  |
| Fremont |  |  |  |  |  |  |  | 69.9 |
| Average | 26.2 | 23.6 | 1.11 | 1.363 | 62.84 | 25.23 | 1.59 |  |
| Std Dev | 2.5 | 3.1 | 0.11 | 0.211 | 7.12 | 2.40 | 0.29 |  |
| No. plants: 19 |  |  |  |  |  |  |  |  |
| Lecanu |  |  |  |  |  |  |  | 74.4 |
| Average | 26.9 | 26.0 | 1.03 | 1.481 | 58.05 | 26.08 | 1.51 |  |
| Std Dev | 2.7 | 2.2 | 0.13 | 0.350 | 4.84 | 4.14 | 0.35 |  |
| No. plants: 26 |  |  |  |  |  |  |  |  |
| Female of Amerigo (fertile) |  |  |  |  |  |  |  | 83.3 |
| Average | 33.8 | 28.3 | 1.19 | 1.267 | 51.96 | 22.74 | 1.18 |  |
| Std Dev | 2.0 | 3.2 | 0.20 | 0.139 | 2.88 | 1.90 | 0.15 |  |
| No. plants: 9 |  |  |  |  |  |  |  |  |
| Female of Amerigo (CMS) |  |  |  |  |  |  |  | 85.0 |
| Average | 31.3 | 27.8 | 1.12 | 1.404 | 51.75 | 23.31 | 1.21 |  |
| Std Dev | 3.1 | 4.1 | 0.17 | 0.405 | 4.50 | 3.50 | 0.29 |  |
| No. plants: 12 |  |  |  |  |  |  |  |  |
| Male of CFL5752 |  |  |  |  |  |  |  | 73.6 |
| Average | 33.7 | 22.2 | 1.52 | 0.798 | 48.25 | 22.77 | 1.10 |  |
| Std Dev | 2.5 | 2.2 | 0.20 | 0.252 | 4.94 | 2.99 | 0.26 |  |
| No. plants: 20 |  |  |  |  |  |  |  |  |
| Handcross 64 |  |  |  |  |  |  |  | 71.6 |
| Average | 31.1 | 21.1 | 1.48 | 1.050 | 54.73 | 24.80 | 1.36 |  |
| Std Dev | 4.0 | 3.9 | 0.32 | 0.338 | 7.55 | 3.50 | 0.34 |  |
| No. plants: 18 |  |  |  |  |  |  |  |  |
| Handcross 14 |  |  |  |  |  |  |  | 76.9 |
| Average | 35.1 | 23.0 | 1.53 | 1.218 | 53.53 | 22.47 | 1.20 |  |
| Std Dev | 4.6 | 3.1 | 0.26 | 0.340 | 6.33 | 2.51 | 0.26 |  |
| No. plants: 20 |  |  |  |  |  |  |  |  |
| New DH line 123 |  |  |  |  |  |  |  | 71.0 |
| Average | 36.1 | 21.8 | 1.66 | 0.810 | 51.83 | 21.22 | 1.10 |  |
| Std Dev | 5.5 | 3.1 | 0.37 | 0.3 | 4.7 | 1.8 | 0.2 |  |
| No. plants: 24 |  |  |  |  |  |  |  |  |

Example 6

Production of a Cauliflower Plant Comprising the Trait of Persistent White Curd The original source of the trait of persistent white curd was an Egyptian landrace derived from Genebank PI 183214. Besides the persitent whiteness, PI 183214 carries many undesirable traits, such as poor curd quality and susceptibility for downy mildew. The original persistent white material was crossed with plants of a cauliflower elite line with good curd quality. The resulting F1 progeny was self-pollinated and the resulting progeny was planted in open fields. The best plants were self-pollinated again. The persitent white plants with the best curd quality and plant habit were selected in the F3 population. These plants were used as a donor of the trait of persistent white curd with better curd quality and plant habit than the original source.

These plants were crossed again with cauliflower plants to further improve plant habit and curd quality. Elite lines were developed from F2 populations derived from these crosses. Plants of broccoli lines were crossed with some of these F2 plants to introduce the trait of long stem, long internode and loose foliage in these plants. Before starting line development, one backcross with plants of a cauliflower line comprising the trait of persistent white curd was performed. Line fixation was carried out using the dihaploid technique.

What is claimed is:

1. A method for producing a cauliflower plant comprising:
   a) crossing a cauliflower plant and a plant of line 03P001, representative seed of which being deposited under accession number NCIMB 41228;
   b) obtaining a progeny plant from the cross of step a);
   c) selecting a plant comprising at maturity a stem with an average internode length of at least 1.25 cm.

2. The method according to claim 1, further comprising obtaining a dihaploid of said progeny plant selected in step c).

3. Seed of a plant of line 03P001, representative seed of which being deposited under accession number NCIMB 41228.

4. Plant grown from a seed of claim 3.

5. Part of a plant of claim 3.

6. The method of claim 1 further comprising (d) a cross between an additional cauliflower plant and a plant selected from the group consisting of the plant obtained in step (b) and the plant selected in step (c).

7. The method of claim 1 further comprising multiple generations of additional crosses made with the plant obtained in step (b) via one of the methods selected from the group consisting of outcrossing to a cauliflower plant other than the cauliflower plant used in step (a), backcrossing to a parent or grandparent of the plant obtained in step (b) and selfing.

8. A plant produced by the method of claim 1.

* * * * *